United States Patent [19]

Anis

[11] Patent Number: 4,804,361

[45] Date of Patent: Feb. 14, 1989

[54] FLEXIBLE ONE-PIECE POSTERIOR CHAMBER LENS

[76] Inventor: Aziz Y. Anis, 7531 N. Hampton, Lincoln, Nebr. 68506

[21] Appl. No.: 44,753

[22] Filed: May 1, 1987

Related U.S. Application Data

[63] Continuation-in-part of Ser. No. 201,388, May 17, 1988, which is a continuation of Ser. No. 624,232, Jun. 25, 1984, abandoned.

[51] Int. Cl.⁴ ............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 4,402,579 | 9/1983 | Poler | 623/6 X |
| 4,494,254 | 1/1985 | Lopez | 623/6 |
| 4,681,586 | 7/1987 | Woods | 623/6 |

FOREIGN PATENT DOCUMENTS

| | | | |
|---|---|---|---|
| 2515956 | 5/1983 | France | 623/6 |
| 8500527 | 1/1986 | Netherlands | 623/6 |
| 2124500A | 2/1984 | United Kingdom | 623/6 |

Primary Examiner—Ronald L. Frinks
Attorney, Agent, or Firm—Vincent L. Carney

[57] ABSTRACT

A posterior chamber lens implant comprising a flexible, substantially ring-shaped position fixation member which extends around a lens body. Flexible connectors connect the lens body with the position fixation member to cause the lens body to be centrally positioned with respect to the implant. The relationship of the position fixation member and the connectors permits the position fixation member to be compressed towards the lens body to enable the implant to be inserted in the eye.

3 Claims, 2 Drawing Sheets

FLEXIBLE ONE-PIECE POSTERIOR CHAMBER LENS

Related Cases

This application is a continuation-in-part of U.S. application Ser. No. 201,388 filed May 17, 1988 for FLEXIBLE POSTERIOR CHAMBER LENS which is a continuation of U.S. application Ser. No. 624,232 filed June 25, 1984, now abandoned, to Aziz Y. Anis.

BACKGROUND OF THE INVENTION

This invention relates to a posterior chamber lens.

The human eye is a very complex organ comprising numerous interacting elements which gather, focus, and transmit light rays to nerve endings which eventually transmit the information to the brain for image perception. The eye includes a natural crystalline lens of avascular tissue, the transparency of which depends upon the critical regularity of its fibers and the balance of its chemical constituents. Obviously, there are enumerable factors which may interfere with lens makeup and thereby affect its transparent character. No matter what the reason, a condition of opacity in the lens, commonly called cataract, reduces the visual performance of the eye. When the visual performance is reduced to an unacceptable level, surgical cataract extraction becomes a necessity.

An eye without a lens, a condition called aphakia, is obviously defective from an optical point of view in as much as it cannot properly refract incident light rays. Aphakic correction may be accomplished in three ways:

(1) thick eye glasses worn in front of the eye;
(2) contact lenses worn on the eye, or
(3) artificial intraocular lens implant within the eye.

It is this latter procedure with which the instant invention is concerned.

The structure and procedure of installing an intraocular lens is very critical because of the elements which make up the eye are extremely sensitive and subject to irreparable damage. Numerous experimental lens designs have been abandoned through the years because they caused corneal damage and other manifestations of intraocular irritation. For example, in the late 1940's and early 1950's, H. Ridley conducted clinical experiments with an artificial intraocular lens which included a lens portion having foot-like projections extending radially away therefrom. This device was placed in the posterior chamber with the feet extending between the ciliary processes and the base of the iris. The lens proved positionally unstable and resulted in unsatisfactory amounts of irritation.

Many attempts have been made to provide a satisfactory intraocular lens. In an effort to remedy the problems associated with the prior art lens implants, applicant previously has been granted U.S. Pat. Nos. 4,143,427; 4,166,293; 4,251,887 and 4,575,374.

Although applicant's previous lens implants did represent a significant advance in the art, it is believed that the instant invention represents further advance in the art in that it does provide a maximum contact of the position fixation element.

Therefore, it is a principal object of this invention to provide an improved posterior chamber lens.

A further object of the invention is to provide a posterior chamber lens wherein a substantially ring-shaped member extends around a centrally positioned lens body with connecting members extending between the lens body and the fixation member.

Yet another object of the invention is to provide a lens of the type described which is of one-piece construction.

Still another object of the invention is to provide a lens of the type described including a ring-shaped position fixation member which may be compressed relative to the centrally positioned lens body to enable the implant to be inserted into the capsular bag.

Still another object of the invention is to provide a posterior chamber lens which will remain in place even if pressure or force is inadvertently applied to one portion of the lens.

These and other objects will be apparent to those skilled in the art.

SUMMARY OF THE INVENTION

Figure 1:
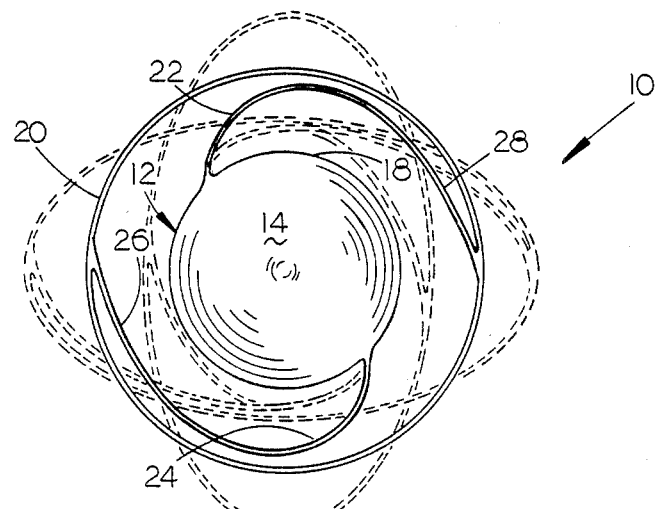
FIG. 1 is an elevational view of one form of the invention with the broken lines indicating various positions of deflection of the position fixation member.

A posterior chamber lens implant is described which may be implanted in the eye after the natural lens of the eye has been removed. In the preferred embodiment of the invention, a flexible, substantially ring-shaped position fixation member extends around a lens body which has a diameter less than the position fixation element. Flexible connection means connects the lens body with the position fixation member to cause the lens body to be centrally positioned with respect to the implant. The means of connecting the lens body to the fixation member also permits the fixation member to be compressed relative to the lens body to facilitate insertion of the implant into the eye. In a modified version of the invention, a pair of spaced-apart posts are substituted for one of the connecting members.

DESCRIPTION OF THE PREFERRED EMBODIMENT

The lens implant of this invention is referred to generally by the reference numeral 10. Lens implant 10 includes a disc-shaped lens body 12 which may either be of the convex-plano or convex-convex configuration. For purposes of description, lens body 12 will be described as having a front face 14, back face 16 and peripheral edge 18.

A ring-shaped position fixation member 20 is positioned outwardly of the lens body 12 and is connected thereto by a pair of elongated curved connecting members 22 and 24 which extend oppositely from the lens body 12. As seen in the drawings, each of the members 22 and 24 have a portion thereof which is generally concentrically positioned with respect to the fixation member 20 and which is referred to generally by the reference numerals 26 and 28 respectively. Preferably, lens body 12 has a diameter of 6 millimeters but the same can be between 4.0 and 8 millimeters. Preferably, the diameter of the ring forming fixation member 20 is 10.5 millimeters but the same can vary between 8.0 millimeters and 13.0 millimeters. Preferably, the diameter of the cross-section through the fixation member 20 is 0.15 millimeters. The construction of the lens implant 10 is such that the ring-shaped fixation member 20 will engage the capsular bag for 360°. The connecting members 22 and 24 aid in centrally positioning the lens body 12 with respect to the fixation member 20. The construction of the lens implant 10 is such that the fixation member 20 may be compressed towards the lens body 12, as illustrated by the broken lines in FIG. 1, to enable the implant 10 to be inserted into the capsular bag.

Figure 3:
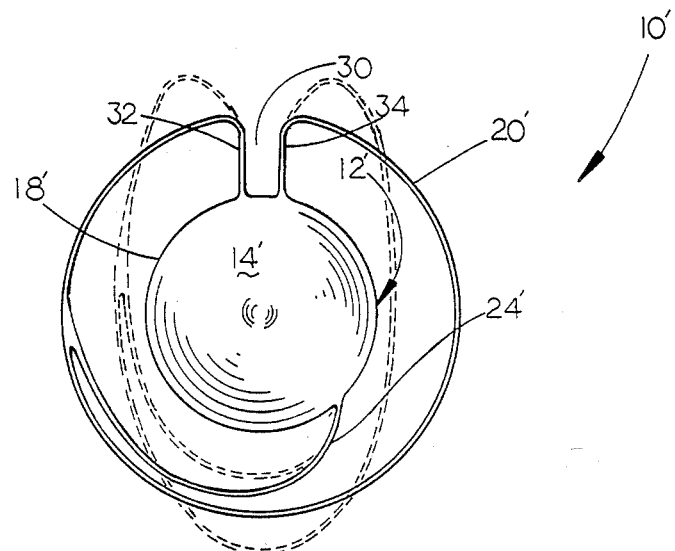
FIG. 3 is a view similar to FIG. 1 except that a modified form of the invention is disclosed.
Figure 4:
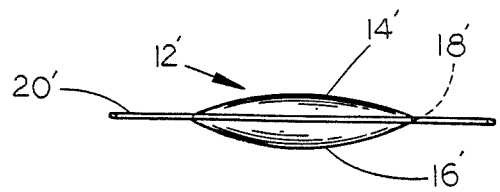
FIG. 4 is an end view of the embodiment of FIG. 3.

In the embodiment shown in FIGS. 3 and 4, the fixation member 20' does not extend completely around the lens body 12' but is provided with a slight gap referred to generally by the reference numeral 30. As seen in FIGS. 3 and 4, a pair of posts 32 and 34 extend radially outwardly from lens body 12' and are connected to the substantially ring-shaped fixation member 20'. A single curved connecting member 24' connects lens body 12' with the member 20' substantially opposite the posts 32 and 34 as seen in the drawings. In the embodiment of FIGS. 3 and 4, the fixation member 20' does engage the structure of the eye for almost 360°. The posts 32 and 34 and the connecting member 24' aid in centrally positioning the lens body 12' with respect to the fixation member 20'. The construction of the lens implant of FIGS. 3 and 4 is substantially the same as the preferred embodiment of this invention in that it does permit the fixation member 20' to be compressed relative to the lens body 12' for insertion into the capsular bag as illustrated by broken lines in FIG. 3.

In all of the embodiments, the lens may be inserted in any position within the eye since there is not a top or bottom portion of the lens implant. The 360° engagement of the fixation member 20 with the eye positively ensures that the lens implant will remain in position and will not become inadvertently dislodged. The lens implant of FIGS. 3 and 4 functions similarly to that of the embodiment previously described.

Figure 2:
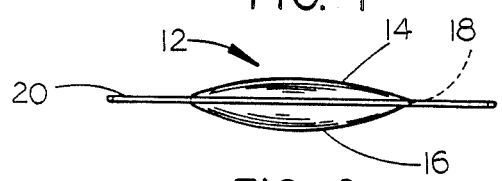
FIG. 2 is an end view of the embodiment of FIG. 1.
Figure 5:
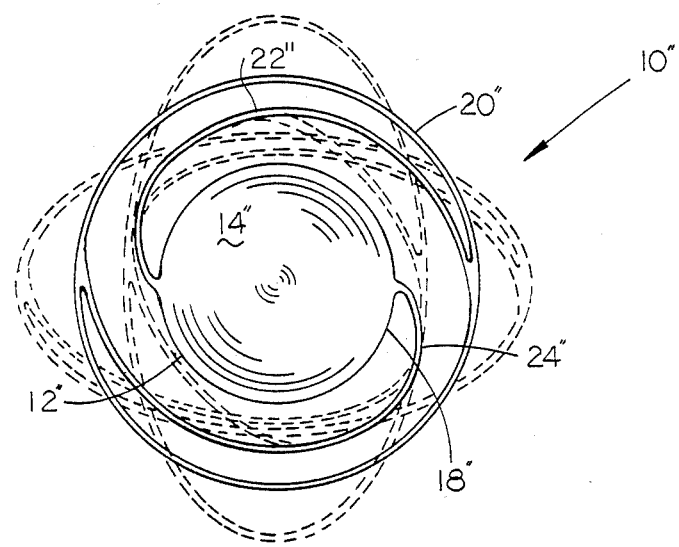
FIG. 5 is a view similar to FIGS. 1 and 3 except that a further modified form of the invention is illustrated.

In the embodiment shown in FIG. 5, the fixation member 20" extends completely around the lens body 12" and is connected thereto by a pair of elongated curved connecting members 22" and 24" which extend oppositely from lens body 12". Essentially, connecting member 24" extends from the three o'clock position to the nine o'clock position while connecting member 22" extends from approximately the nine o'clock position to the three o'clock position. The embodiment of FIG. 5 is substantially the same as that shown in FIGS. 1 and 2 except that the connecting members are slightly longer and have a longer portion of their length concentric to the periphery of the lens body.

In all of the embodiments, the fixation members may dwell in the same plane as the lens body as illustrated in the drawings or they may be offset therefrom.

Thus it can be seen that the invention accomplishes at least all of its stated objectives.

I claim:

1. A one-piece intraocular lens implant, comprising:
a flexible, substantially ring-shaped position fixation member,
a disc-shaped lens body having a diameter less than said position fixation member and being positioned within said position fixation member,
and flexible connection means connecting said lens body with said position fixation member,
said flexible connection means including a pair of elongated members extending generally oppositely from said lens body, at least one of said elongated members having a substantial portion of its length substantially concentrically disposed alongside said position fixation member.

2. A one-piece intraocular lens implant, comprising:
a flexible substantially ring-shaped position fixation member,
a lens body having a diameter less than said fixation member and being positioned within said fixation member,
and flexible connection means connecting said lens body with said fixation member, wherein said flexible connection means comprises a pair of closely spaced-apart posts extending from said lens body to said position fixation member and at least one elongated curved member extending from said lens body to said position fixation element.

3. A one-piece intraocular lens implant, comprising:
a flexible, substantially ring-shaped position fixation member;
a lens body having a diameter less than said position fixation member and being positioned within said position fixation member;
and flexible connection means connecting said lens body with said position fixation member and adapted to flex said fixation member into a substantially elliptical shape when a radially-directed compressive force is applied to diametric points on said fixation member, whereby the lens may be squeezed into an elliptical shape and inserted through an opening smaller than the diameter of the ring-shaped fixation member;
said fixation member being a closed, circular ring.

* * * * *